United States Patent
Mahalingam et al.

(10) Patent No.: US 7,189,419 B2
(45) Date of Patent: Mar. 13, 2007

(54) USE OF ACTIVE EXTRACTS TO LIGHTEN SKIN, LIPS, HAIR, AND/OR NAILS

(75) Inventors: Harish Mahalingam, Ledgewood, NJ (US); Brian C. Jones, Flower Mound, TX (US); Nicole McCain, Lexington, VA (US); Pornngarm Limtrakul, Chiang Mai (TH)

(73) Assignee: Avon Products, Inc., New York, NY (US)

( * ) Notice: Subject to any disclaimer, the term of this patent is extended or adjusted under 35 U.S.C. 154(b) by 129 days.

(21) Appl. No.: 10/321,706

(22) Filed: Dec. 17, 2002

(65) Prior Publication Data

US 2004/0115146 A1 Jun. 17, 2004

(51) Int. Cl.
*A01N 65/00* (2006.01)
(52) U.S. Cl. .................................... 424/725
(58) Field of Classification Search ................. 424/725
See application file for complete search history.

(56) References Cited

U.S. PATENT DOCUMENTS

| | | | |
|---|---|---|---|
| 4,745,186 A | 5/1988 | Mudd et al. ................. 536/119 |
| 5,609,875 A * | 3/1997 | Hadas ......................... 424/757 |
| 5,698,423 A | 12/1997 | Holowach-Keller et al. ..... 435/119 |
| 5,756,099 A | 5/1998 | Simpson ................... 424/195.1 |
| 5,858,371 A * | 1/1999 | Singh et al. .................. 424/731 |
| 5,980,904 A | 11/1999 | Leverett et al. ........... 424/195.1 |
| 6,248,309 B1 | 6/2001 | Iyer et al. ..................... 424/49 |
| 6,387,370 B1 | 5/2002 | Yegorova ................... 424/94.2 |
| 6,417,157 B1 | 7/2002 | Wadsworth et al. ........... 512/5 |
| 6,673,377 B1 | 1/2004 | Cherdshewasart .......... 424/725 |
| 2003/0064039 A1 * | 4/2003 | Kolodziej et al. ............ 424/63 |
| 2004/0053791 A1 * | 3/2004 | Langer et al. ............... 508/154 |
| 2004/0067245 A1 * | 4/2004 | Mahalingam et al. ........ 424/401 |
| 2004/0076650 A1 * | 4/2004 | Blin et al. ................... 424/401 |

FOREIGN PATENT DOCUMENTS

| | | |
|---|---|---|
| JP | 7-25742 | 1/1995 |
| JP | 7-187989 | 7/1995 |
| JP | 10-265322 | 10/1998 |
| JP | 2001-163759 | 6/2001 |
| JP | 2001-181173 | 7/2001 |
| WO | WO 02/36363 | 5/2002 |
| WO | WO 02/36364 | 5/2002 |
| WO | WO 02/41855 | 5/2002 |

OTHER PUBLICATIONS

Srivastava et al., Natural Product Sciences, 8(3), pp. 83-89, 2002.*
Dimri et al., Indian Journal of Animal Sciences , 71, (12), 1145-51, Dec. 2001.*
Badam, "In vitro studies on the effect of glycyrrhizin from Indian glycyrrhiza linn. On some RNA and DNA Viruses, " Indian Journal of Pharmacology, 1994; 26: 194-199.
Mengi et al., "Evaluation of ocular anti-inflammatory activity of burea frondosa." Indian Journal of Pharmacology, 1995; 27: 116-119.

* cited by examiner

*Primary Examiner*—Michael Meller
(74) *Attorney, Agent, or Firm*—Ohlandt, Greeley, Ruggiero & Perle, L.L.P.

(57) ABSTRACT

There is provided a composition having at least one of the following active extracts *Butea frondosa, Naringi crenulata, Stenoloma chusana*, or any combinations thereof. There is also provided a composition having at least one of the following additional extracts *Azadirachta indica, Glycyrrhiza glabra linn., Morinda citrifolia*, tomato glycolipid or any combinations thereof in combination with one or more of the active extracts. The compositions and methods of the invention are effective to lighten hair, skin, lips and/or nails.

14 Claims, No Drawings

USE OF ACTIVE EXTRACTS TO LIGHTEN SKIN, LIPS, HAIR, AND/OR NAILS

BACKGROUND OF THE INVENTION

1. Field of the Invention

The present invention relates to compositions and methods for lightening the skin, lips, hair, and/or nails. More particularly, the present invention relates to biologically active extracts for lightening the skin, lips, hair, and/or nails.

2. Description of the Related Art

Consumers have sought to lighten and reduce pigmentation in the hair, skin, and nails. There is a need for products that effectively lighten and reduce pigmentation in the hair, skin, and nails. Common applications for such products include, for example, bleaching hyperpigmented hair, skin, and/or nails; reducing age spots; evening or optimizing skin discoloration; improving the appearance of dark circles under the eyes; treating melasma, cholasma, freckles, afterburn scars, and post-injury hyperpigmentation; bleaching hair on the scalp, legs, face, and other areas where bleaching and color reduction are desired; and bleaching nail stains.

Skin, hair and nail pigmentation is determined by the level of melanin present in the epidermis, hair fiber, and nail bed, respectively. Three different types of melanin are present in the epidermis: DHI-melanin, DHICA-melanin and pheomelanin. The different types of melanin vary in color or shade. DHI-melanin is the darkest, and is blackish in color. DHICA-melanin is brownish in color. Pheomelanin is the lightest, and is reddish in color.

Melanin is synthesized in specialized organelles called melanosomes within pigment-producing cells (melanocytes). Melanocytes respond to stimuli to regulate melanin synthesis.

Many substances have been applied to the skin to lighten the skin. Such substances include hydroquinone, kojic acid, licorice and/or its derivatives, ascorbic acid and/or its derivatives, arbutin, bearberry, *Glycyrrhiza glabra* and its derivatives, *Chlorella vulgaris* extract, perilla extract, and coconut fruit extract. Perilla extract is disclosed as a whitening agent in U.S. Pat. No. 5,980,904 and Japanese Publications Nos. 07025742, 07187989, 10265322, 2001163759, and 2001181173. Coconut fruit extract is disclosed as a whitening agent in Japanese Patent No. 2896815B2. An extract of spongy mass of coconut tissue is employed in a tanning sunscreen composition in U.S. Pat. No. 5,756,099.

Active ingredients derived from plants and plant seeds have been employed in topical compositions for a myriad of medicinal, therapeutic and cosmetic purposes. Such active ingredients can be obtained from various parts of a plant such as seeds, needles, leaves, roots, bark, cones, stems, rhizomes, callus cells, protoplasts, organs and organ systems, and meristems. Such active ingredients are incorporated in such compositions in a variety of forms. Such forms include a pure or semi-pure component, a solid or liquid extract or derivative, or a solid plant matter. Plant matter may be incorporated in a variety of subforms such as whole, minced, ground or crushed.

Extracts of *Azadirachta indica*, the neem tree, as well as other plants in the family Meliaceae, are known to have insecticidal activity. Azadirachtin, a major active ingredient of many of these extracts, is a liminoid of the tetranortriterpenoid type useful in commercial insecticides. Tetranortriterpenoids have been shown to be a potent insect growth regulator and feeding deterrent. Methods for producing azadirachtin concentrates from neem seed materials are known in the art. U.S. Pat. No. 5,698,423 to Holowach-Keller et al. is directed to a method for producing azadiractin by cell culture of *Azadiracta indica*.

Extracts of *Glycyrrhiza glabra linn*. are derived from the herb, which grows perennially in subtropical and warm temperate regions. *Glycyrrhiza glabra linn*., commonly known as licorice, has been used in food sweetening. The root extract contains glycyrrhizic acid and glycyrrhetinic acid. The glycyrrhizic acid is known to have an anti-inflammatory effect. The extract of the licorice root and glycyrrhetinic acid have been shown to have desoxycorticosterone and ACTH-like effects. It has been used as a demulcent and mild expectorant. In vitro studies have shown the antiviral properties of both glycyrrhetinic acid and glycyrrhizin (See Badam, "In Vitro Studies on the Effect of Glycyrrhizin from *Glycyrrhiza glabra linn*. on Some RNA and DNA Viruses," Ind. J. Pharma., 26, 194–199 (1994)). The extracts of *Glycyrrhiza glabra linn*. can be extracted by a method disclosed in U.S. Pat. No. 6,248,309 to Iyer, et al.

Extracts of *Morinda citrifolia* are derived from the Indian Mulberry plant. *Morinda citrifolia* has been used in compositions for reducing oxysterol buildup in the blood and normalizing cholesterol and blood pressure in mammals as set forth in U.S. Pat. No. 6,387,370 to Yegorova. A method of extracting and purifying an essential oil product of *Morinda citrifolia* is disclosed in U.S. Pat. No. 6,417,157 to Wadsworth et al.

Extracts of tomato glycolipid are derived from tomato fruit. Methods of extracting and synthesizing tomato glycolipids are disclosed in U.S. Pat. No. 4,745,186 to Mudd et al.

Extracts of *Butea frondosa*, also known as *Butea monosperma*, are derived from an East Indian deciduous tree. *Butea frondosa* has been used as an astringent and in treating diarrhea, dysentery, and pyrosis. Use of *Butea frondosa* for its ocular anti-inflammatory activity has recently been tested (See Mengi, "Evaluation of Ocular Anti-Inflammatory Activity of *Butea frondosa*," Ind. J. Pharma. 27, 116–119 (1995)).

Extracts of *Naringi crenulata*, also known as *Limonia crenulata*, are derived from a small tree indigenous to East India.

*Stenoloma chusana* is a perennial herb found in southeast Asia. Extracts from this plant are known to have uses in treating colds, influenza, bronchitis, burns, cuts, and skin sores (See A Barefoot Doctor's Manual, Running Press, Philadelphia, Pa., p. 638).

Heretofore, these extracts have not been used as an active ingredient in a composition for the purpose of lightening skin, lips, hair or nails.

It would be desirable to have compositions that employ new biological extracts that provide effective levels of lightening, bleaching, hypopigmenting, whitening and/or depigmenting (hereinafter referred to individually and collectively as "lightening" or "lighten"). It would further be desirable to have compositions that are effective in lightening hair, skin, lips, and/or nails and require minimal concentrations of the biological material.

SUMMARY OF THE INVENTION

It is an object of the present invention to provide compositions for lightening of hair, skin, lips, and/or nails having an active plant extract, preferably an active biological plant extract.

It is another object of the present invention to provide such compositions for lightening hair, skin, lips, and/or nails having a minimal amount of an active plant extract.

It is still another object of the present invention to provide such compositions for lightening hair, skin, lips, and/or nails that is suitable for topical application to the hair, skin, lip, and/or nails.

It is yet another object of the present invention to provide compositions for lightening hair, skin, lips, and/or nails that is suitable for oral ingestion.

It is a further object of the present invention to provide methods of lightening hair, skin, lips, and/or nails that include topically applying such compositions to hair, skin, lips and/or nails.

These and other objects and advantages of the present invention are provided by compositions for lightening hair, skin, lips, and/or nails, which compositions have an effective amount of at least one of the following active extracts: *Butea frondosa, Naringi crenulata, Stenoloma chusana*, or any combinations thereof. There is also provided compositions for lightening hair, skin, lips, and/or nails having an effective amount of at least one of the active extracts, and an effective amount of at least one of the following additional extracts: *Azadirachta indica, Glycyrrhiza glabra Linn., Morinda citrifolia*, tomato glycolipid, or any combinations thereof. The present invention also provides methods for lightening hair, skin, lips, and/or nails comprising topically applying or orally ingesting any one of these compositions.

DETAILED DESCRIPTION OF THE INVENTION

The present invention provides compositions for lightening hair, skin, lips, and/or nails. The compositions are preferably topical compositions for application to the hair, skin, lips, and/or nails. However, the present compositions can be for oral ingestion. In either application, the compositions result in a lightening of the hair, skin, lips and/or nails.

The compositions have one or more of the following extracts, as an active biological plant extract or ingredient(s) or in an active amount: *Butea frondosa, Naringi crenulata, Stenoloma chusana*, or any combinations thereof. It has been unexpectedly found that these active extracts reduce pigmentation and lighten hair, skin, lips, and/or nails. In particular, these active extracts have been unexpectedly shown to decrease melanin production and decrease hypermelanocytic states.

It has now been also found that the addition of at least one of these active extracts, namely *Butea frondosa, Naringi crenulata, Stenoloma chusana*, or any combinations thereof, to at least one of the following other or additional extracts, namely *Azadirachta indica, Glycyrrhiza glabra linn., Morinda citrifolia*, tomato glycolipid, or any combinations thereof, can reduce melanin pigmentation of hair, skin, lips and/or nails.

Lightening of hair, skin, lips and/or nails, as used in the present invention, means one or more of the following benefits is achieved. These benefits include bleaching hyperpigmented hair, skin, lips, and/or nails; reducing age spots; evening or optimizing skin discoloration; improving the appearance of dark circles under the eyes; treating melasma, cholasma, freckles, after-burn scars, and post-injury hyperpigmentation; bleaching hair on the scalp, legs, face, and other areas where bleaching and color reduction are desired; and bleaching nail stains.

In its broadest aspects, the present invention is not limited by any particular characterization of the physiological and/or chemical effects of lightening extract or agents. However, the lightening extract used in the present compositions and methods are believed to reduce melanin in hyperpigmented areas by decreasing dark pigment formation in melanocytes and shifting the melanin synthesis path towards light melanin formation by decreasing melanocyte pH, and/or direct chelation of metals involved in melanin synthesis or staining, for example, copper.

In a preferred embodiment of the present invention, the composition, which lightens hair, skin, lips, and/or nails, has an effective amount of at least one of the following active extracts: *Butea frondosa, Naringi crenulata, Stenoloma chusana*, or any combinations thereof. An effective amount means that the one or more active extracts are present at about 0.001 percentage by weight (wt %) to about 20 wt % based on the total weight of the composition. The one or more active extracts are present preferably at about 0.05 wt % to about 10 wt %, and more preferably at about 0.5 wt % to about 5 wt %, based on the total weight of the composition. Most preferably, the one or more active extracts are present in an amount about 1 wt % or less based on the total weight of the composition.

As stated above, in another preferred embodiment of the present invention, the composition for lightening hair, skin, lips, and/or nails has an effective amount of at least one of the active extracts, and one or more of the following other or additional extracts: *Azadirachta indica, Glycyrrhiza glabra linn., Morinda citrifolia*, tomato glycolipid, or any combinations thereof, to synergistically enhance the whitening activity of the composition.

When combined with one or more of the additional extracts, the active extracts are present in the present compositions in an amount about 0.001 wt % to about 10 wt %, and the one or more additional extracts in an amount about 0.05 wt % to about 10 wt %, based on the total weight of the composition. Preferably, the active extracts are present in an amount about 0.05 wt % to about 10 wt % and the one or more additional extracts in an amount about 0.5 wt % to about 5 wt % based on the total weight of the composition. Most preferably, the one or more active extracts are present in an amount equal to or less than about 1 wt %, and the one or more additional extracts are present in an amount equal to or less than 1 wt %, based on the total weight of the composition.

The compositions of the present invention can be used with a carrier or vehicle. The vehicle can be altered to be appropriate for the specific use of the composition without altering the beneficial lightening effects achieved by the use of the one or more active extracts set forth above. The vehicles that can be used in compositions of the present invention include, but are not limited to, water; vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones and polysiloxanes; hydrocarbon oils such as mineral oil, petrolatum, isoeicosane and polyisobutene; polyols such as propylene glycol, glycerin, butylene glycol, pentylene glycol and hexylene glycol; or any combinations thereof.

Preferably, the vehicle is present in an amount about 50 wt % to about 99.8 wt % based on the total weight of the composition. More preferably, the vehicle is present in an amount about 80 wt % to about 99.5 wt % based on the total weight of the composition.

The present compositions may also include one or more of the following ingredients: anesthetic, anti-allergenic, anti-fungal, antimicrobial, anti-inflammatory agent, antioxidant, antiseptic, chelating agent, colorant, depigmenting agent, emollient, emulsifier, exfollient, film former, fragrance, humectant, insect repellent, lubricant, moisturizer, pharmaceutical agent, photostabilizing agent, preservative, skin protectant, skin penetration enhancer, sunscreen, stabilizer, surfactant, thickener, viscosity modifier, vitamin, or any combinations thereof. Preferably, these ingredients are present in an amount about 0.001 wt % to about 10 wt %, based on the total weight of the composition.

The present compositions may also include skin whiteners. Some examples of such suitable skin whiteners include, but are not limited to, one or more of the following: ascorbyl glucoside, vitamin C, retinol and/or its derivatives, arbutin, bearberry extract, rumex crispus extract, milk proteins including hydrolyzed milk proteins, N,N,S-tris(carboxymethyl)cysteamine, oleanolic acids, perilla oil, placenta extract, *saxifragia sarmentosa*, perilla extract, juniperic acid, TDPA, *ligusticum chiangxiong hort., asmunda japonica thunb., stellaria medica* (L.) cyr., *sedum sarmentosum bunge, ligusticum lucidum Ait., ilex purpurea hassk*, emblica, apigenin, ascorbyl palmitol, carruba polyphenols, hesperitin, hydroquinone, inabata polyphenol, isoliquirtigenin, kaempherol-7-neohesperidose, L-mimosine, luteolin, oil-soluble licorice extract P-T(40), oxa acid, phenyl isothiocyanate, cococin, silymarin, T4CA, teterahydro curcumin, unitrienol, ursolic-oleanolic acid, UVA/URSI, or any combinations thereof.

The compositions of the present invention can be formulated in any suitable product form. Such product forms include, but are not limited to, aerosol spray, cream, dispersion, emulsion, foam, gel, liquid, lotion, mousse, ointment, patch, pomade, powder, pump spray, solid, solution, stick, and towelette.

The present compositions provide for products, especially cosmetic products that improve lightening of skin, nail, lips, and/or hair. Also, the present compositions can be formulated to deliver a consistent level of an active ingredient, or blend of ingredients, so that a desired cosmetic effect is achieved.

The following are examples of the present invention.

EXAMPLE 1

Melanosome Uptake Assay (*Stenoloma chusana* and *Naringi crenulata*) was done as follows. Confluent cultures of B16 melanocytes produce moderate levels of melanosomes. However, to induce elevated melanosome production in this cell line, semi-confluent (60%) cultures of B16 cells were treated for approximately thirty-six (36) hours with normal growth medium supplemented with 10 mm ammonium chloride (final conc.). The medium was then aspirated and the hypermelanotic cells were washed (2×2 ml) with distilled water to provide a hypotonic stress to the cells. An aliquot (2 ml) of a hypotonic lysis solution (0.02% NP-40 in water) was added to each plate and the plates were incubated for approximately five (5) minutes at room temperature. Following verification of cell lysis using light microscopy, the cellular material from three (3) culture plates were pooled in a 15 ml conical tube and centrifuged (200×g) for 5 minutes to remove cellular debris. The resulting supernatant containing melanosomes was transferred to a clean 15 ml conical tube and centrifuged (850×g) for twenty (20) minutes. The resulting pellet containing the isolated melanosomes were resuspended in 1 ml of Phosphate Buffered Saline (PBS) and stored at 4° C. until used.

The treatment of keratinocytes with melanosomes was measured as follows. The normal human epidermal keratinocytes (NHEKs) (available from Clonetics, Inc.) were plated in the wells of 24-well plates at a density of 200,000 cells/well. Approximately twenty-four (24) hours later, the growth medium was replaced with 1 ml of the appropriate growth medium (i.e., DMEM/KGM-2) containing the melanosome preparation with or without additional treatment conditions. The cells were treated with different concentrations of the active materials (powder form or aqueous form). The cells were then returned to the incubator for approximately one and one-half (1.5) hours. For these studies, each well of keratinocytes was treated with the amount of melanosomes isolated from a single plate of B16 cells.

In some experiments, the 24 well plates of treated keratinocytes were centrifuged for 15 minutes at 1,000 rpm to facilitate the deposition of the melanosomes onto the surface membranes of the keratinocytes. The plates were then returned to the incubator for 1.25 hours.

For the analysis of melanosome uptake, the cells in each well of keratinocytes were rinsed (3×1 ml) with PBS, removed from the plate using trypsin/EDTA, and washed with PBS. To analyze the uptake of melanosomes by the keratinocytes, the internalized melanin was extracted from the cells according to a modified method of Bessou-Touya, S., et al. (Chimeric Human Epidermal Reconstructs To Study The Role Of Melanocytes And Keratinocytes In Pigmentation And Photoprotection. J. Invest. Dermatol., 111:1103–1108, 1998) and quantified spectrophotometrically by determining the melanin-specific absorbance at 405 nm.

The melanocytes synthesize melanin and deposits onto melanosomes. Visual manifestation of skin color is due to presence of melanin/melanosomes in keratinocytes. Melanosomes are taken up by keratinocytes and the rate of uptake, retention and processing of melanosomes in the keratinocytes is a key determinant of skin color. The internalized melanin value reflects the amount of melanin/melanosome uptake and retention by the keratinocytes. Thus, the lower internalized melanin values, particularly internalized melanin values that are less than the control with melanin, indicate that melanin uptake by the keratinocytes has been inhibited.

The results are as follows. At 0.5% volume/volume, *Stenoloma chusana* showed a 44% decrease in melanosome uptake as compared to the positive control. At 0.5% volume/volume, *Naringi crenulata* showed a 39% decrease in melanosome uptake as compared to the positive control.

EXAMPLE 2

For B16 assay (*Naringi crenulata*), the actives were tested in monolayer cell culture of B16 mouse melanoma cells. These cells constitutively produce melanin and are a model system for monitoring the inhibition of melanin synthesis. The cells were seeded into 96-well plates at 5×10³ cells/well and culture attached for twenty-four (24) hours. The media were then replaced with fresh media containing plant extracts. The active material was applied to six (6) wells of B16 cells on 96-well plates to allow statistical analysis. The cells were dosed with medium alone as the negative control, or the test article for seven (7) days. The plates were read at 540 nm to detect melanin formation. An increase in absorbance at 540 nm reflects a higher melanin content in the well.

At 0.05% weight/volume, *Naringi crenulata* showed a 61% decrease in pigmentation as compared to the positive control.

EXAMPLE 3

For $^{14}$C-Dopa incorporation (*Butea frondosa*), melanogenic activity was measured by measuring the radioactive melanin formed as $^{14}$C DOPA is converted to the acid insoluble melanin biopolymer in B16F10 melanoma cells. Cells were seeded into 24-well plates at a density of $2 \times 10^4$ cells per well and cultured attached for forty-eight (48) hours. The media were then replaced with fresh media containing plant extracts and 0.2 μCi of $^{14}$C DOPA. The cells were further incubated for 24 hours. After incubation, media were discarded and the cells were rinsed with PBS, lysed by adding 0.125 ml of 1N NaOH and incubated at 37° C. for 30 minutes, and then neutralized with 0.025 ml of 5N HCL. The resulting cell lysates were transferred into liquid scintillation vials and mixed with scintillation cocktail, and the radioactivity was determined by scintillation counter. A portion of the cell lysates was kept and the protein content was determined by Lowry method. The results were normalized to the amount of protein determined for each assay.

At 0.005% weight/volume, *Butea frondosa* showed a 22% decrease in $^{14}$C DOPA conversion as compared to the positive control.

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of lightening hair, skin, lips and/or nails, comprising topically applying to an area of human skin, hair, lips and/or nails in need of lightening an effective amount of a cosmetic composition having at least one extract selected from the group consisting of *Butea frondosa, Naringi crenulata*, and *Stenoloma chusana*.

2. The method of claim 1, wherein the composition further comprises a vehicle, wherein the at least one extract is present in an amount about 0.001 wt % to about 20 wt % based on the total weight of the composition.

3. The method of claim 1, wherein the composition further comprises a vehicle, wherein the at least one extract is present in an amount about 0.05 wt % to about 10 wt % based on the total weight of the composition.

4. The method of claim 1, wherein the composition further comprises a vehicle, wherein the at least one extract is present in an amount about 0.5 wt % to about 5 wt % based on the total weight of the composition.

5. The method of claim 1, further comprising at least one additional extract selected from the group consisting of *Azadirachta indica, Glycyrrhiza glabra linn., Morinda citrifolia*, and tomato glycolipid.

6. The method of claim 1, wherein the composition is applied to the skin.

7. The method of claim 2, wherein the composition is applied to the skin.

8. The method of claim 3, wherein the composition is applied to the skin.

9. The method of claim 4, wherein the composition is applied to the skin.

10. The method of claim 5, wherein the composition is applied to the skin.

11. The method of claim 10, wherein the at least one extract and the at least one additional extract are together present in an amount about 0.001 wt % to about 20 wt % based on the total weight of the composition, wherein the at least one additional extract is *Azadirachta indica*.

12. The method of claim 10, wherein the at least one extract and the at least one additional extract are together present in an amount about 0.001 wt % to about 20 wt % based on the total weight of the composition, wherein the at least one additional extract is *Glycyrrhiza glabra linn*.

13. The method of claim 10, wherein the at least one extract and the at least one additional extract are together present in an amount about 0.001 wt % to about 20 wt % based on total weight of the composition, wherein the at least one additional extract is *Morinda citrifolia*.

14. The method of claim 10, wherein the at least one extract and the at least one additional extract are together present in an amount about 0.001 wt % to about 20 wt % based on the total weight of the composition, and wherein the at least one additional extract is tomato glycolipid.

* * * * *